United States Patent [19]

Ishihara

[11] Patent Number: 5,527,784
[45] Date of Patent: Jun. 18, 1996

[54] **ANTIHYPERLIPIDEMIC AND ANTIOBESITY AGENT COMPRISING LEVAN OR HYDROLYSIS PRODUCTS THEREOF OBTAINED FROM *STREPTOCOCCUS SALIVARIUS***

[76] Inventor: Kazuoki Ishihara, 3-2-6-407, Minami Osawa, Hachioji-shi, Tokyo, Japan

[21] Appl. No.: 357,770

[22] Filed: Dec. 16, 1994

Related U.S. Application Data

[62] Division of Ser. No. 81,604, Jun. 8, 1993, abandoned.

[30] Foreign Application Priority Data

Jun. 10, 1992 [JP] Japan .................................. 4-194472

[51] Int. Cl.⁶ ........................ A01N 43/04; A61K 31/715
[52] U.S. Cl. ............................. 514/54; 536/119; 435/885
[58] Field of Search ............................. 514/54; 536/119; 435/885

[56] References Cited

U.S. PATENT DOCUMENTS

| | | | |
|---|---|---|---|
| 4,520,017 | 5/1985 | Tunc | 424/79 |
| 4,623,539 | 11/1986 | Tunc | 424/79 |
| 4,871,574 | 10/1989 | Yamazaki et al. | 426/622 |

OTHER PUBLICATIONS

Khorramian BA et al, Carbohyor. Res. 108(1):1–12 (1982).
Iseki M. et al, Mem Osaka Kyoiku Univ III Nat Sci Appl Sci 28(2–3):87–96 (1980).
Cho S et al, Fukuoka Joshi Daigaku Kaseigaku Bu Kiyo 16:65–9 (1985).
Stefanovich V, Res. Comm. Chem. Path. Pharm. 7:557–571 (1974).
Takeno, et al., "Effect of Partially Decomposed Guar Gum on High–Cholesterol–fed Rats and Non–dietary Fiber–fed Rats" (*J. Jpn. Soc. Nutr. Food Sci.*) 43, pp. 421–425 (1990) (Abstract).
"Physio–Chemical Characteristics of the Levan Produced By *Streptococcus salivarius*" by E. Newbrun and S. Baker, Carbohyd. Res., (1968) pp. 165–170.

*Primary Examiner*—Michael G. Wityshyn
*Assistant Examiner*—S. Saucier
*Attorney, Agent, or Firm*—Meltzer, Lippe, Goldstein et al.

[57] ABSTRACT

The present invention relates to an antihyperlipidemic and antiobesity agent which has levan and/or a partial hydrolysate of levan as its active ingredient in order to provide an agent which can suppress increases in lipids in the blood serum and increases in body fat even when high-calorie foods such as carbohydrates are eaten; and at the same time, it is easy to take in effective quantities and there are no adverse side effects or toxicity.

10 Claims, No Drawings

ANTIHYPERLIPIDEMIC AND ANTIOBESITY AGENT COMPRISING LEVAN OR HYDROLYSIS PRODUCTS THEREOF OBTAINED FROM *STREPTOCOCCUS SALIVARIUS*

This is a division of application Ser. No. 08/081,604, filed Jun. 8, 1993 now abandoned.

BACKGROUND OF THE INVENTION

1. Field of the Invention

The present invention relates to an antihyperlipidemic and antiobesity agent which can be used in foods, drugs or animal feed.

2. Description of Prior Art

The known drugs that may be used to reduce the quantity of lipids in blood serum are: nicotinic acid and its derivatives, cholesterol synthesis inhibitors, Probucol and so forth. Also, water-soluble dietary fibers such as vegetable gums, including pectin, are food constituents that are known to have the effect of improving lipid metabolism. However, adverse side effects such as hot flashes, itchiness, and muscular impairment have been reported when the above mentioned antihyperlipidemics are used, and they have not yet been proved to be safe. Moreover, for an adult to obtain an appreciable lipid lowering effect or a significant improvement in lipid metabolism, the water-soluble dietary fibers mentioned above, such as vegetable gums, including pectin, must be taken in quantities of 10 grams to several tens of grams per day. It is extremely difficult to take a solution of vegetable gum such as pectin in such great quantities, .however, because of its high viscosity. In practice, therefore, it is almost impossible to take dietary fibers in aqueous solution in sufficient quantities on a daily basis.

It should be noted that the viscosity of water-soluble dietary fibers can be reduced by partial hydrolysis. As an example of reducing viscosity through partial hydrolysis in this manner, material and results of animal experiments with guar gum have been reported (F. Takeo et al., 'Effect Of Partially Decomposed Guar Gum on High-Cholesterol-fed Rats and Non-dietary Fiber-fed Rats', Journal of Japan Society of Nutrition and Food Journal, Vol. 43 #6 pp 421–425, 1990). According to this report, the hydrolysate that results from partial hydrolysis of guar gum has a lower viscosity than guar gum itself, but still it is quite viscous. Also, in order to obtain significant improvement in lipid metabolism, the guar gum hydrolysate must constitute 5% (dry-weight) of the total volume of food consumed. Therefore, in practice, it is nearly impossible to achieve a significant improvement in lipid metabolism by consuming water-soluble dietary fibers, even if they are partially hydrolyzed.

Imbibitional dietary fibers such as mannan and non-digesting sweeteners such as glycyrrhetinic acid, stevioside and aspartame (L-aspartyl-L-phenylalanine methylester) are low-calorie food materials that are used for preventing obesity. These non-digesting sweeteners are used as a replacement for sucrose. The quantity of carbohydrates absorbed in the body is reduced as a result, and such non-digesting sweeteners are, therefore, thought to have the effect of reducing the quantity of lipids in the blood serum as well as the effect of metabolizing lipids that have accumulated in the body. However, because of the significant deleterious effect that such non-digesting sweeteners have on the flavor and texture of food, these sweeteners cannot be used in great quantities. In any case, it is difficult to avoid the large quantities of natural sugars such as sucrose and fructose that are present in fruit and many other foods. Thus, the strategy of trying to replace sugar in the diet with non-digesting sweeteners is, on the whole, a very limited one for reducing the intake of sugars.

This invention is an antihyperlipidemic and antiobesity agent which can suppress increases in lipids in the blood serum and increases in body fat even when high-calorie foods such as carbohydrates are eaten. At the same time, it is easy to take in effective quantities and there are no adverse side effects or toxicity.

SUMMARY OF THE INVENTION

The antihyperlipidemic and antiobesity agent in the present invention has levan and/or a partial hydrolysate of levan as its active ingredient.

DETAILED DESCRIPTION OF THE INVENTION

The antihyperlipidemic and antiobesity agent in the present invention has levan and/or a partial hydrolysate of levan as its active ingredient. The levan is produced by bacteria such as the *Streptococcus salivarius* and *Bacillus subtilis*, etc. It is also produced by the enzymes (levan sucrase) that are produced by these bacteria. The partial hydrolysate of levan is prepared by acid hydrolysis of levan under mild conditions.

Outstanding antihyperlipidemic effects, normalization of cholesterol metabolism and inhibition of increases in neutral lipids in the blood serum and body fat were observed when both levan and partial hydrolysate of levan were given to animal experiment with dosage levels at less than one third of the dosage levels required for vegetable gum. Also, even though it is a macromolecule with a molecular weight of more than $10^7$, levan has relatively low viscosity. The viscosity of a 5% aqueous solution at 25° C. is 4.5 cp. Its partial hydrolysate has even lower viscosity. The viscosity of a partial hydrolysate with a molecular weight of 1500–4000 in a 10% aqueous solution at 25° C. is 2 cp. Therefore, since viscosity does not present any problems for taking the substance orally, it is easily taken in large quantities.

The levan and partial hyrolysate of levan of the present invention are used in the following methods and dosages: that is, levan and partial hyrolysate of levan may be prepared .in various forms of edible compositions such as tablets, capsules, granulated powders, drinks, processed foods and so forth. The dosages should be a minimum of 1 mg/kg of body weight per day, preferably 100 mg/kg of body weight or more than per day. No upper limit for dosage has been specifically defined, although we would assume that it would be extremely difficult to take more than 2 g/kg.

EXAMPLES

In these examples of implementation, levan and partial hyrolysate of levan were obtained by the method described below. However, the present invention does not restrict applicable levans to those levans obtained through the production method described here. Levans obtained through other microorganisms and enzymes and also levans obtained through synthesis can be used as well. Partial hydrolysates of levan also may be obtained by methods other than the production method described below. The levan used here was obtained through the method described in Physiochemical Properties of Levan Produced With *Streptococcus sali-*

*varius* by Newbrun and Baker in Carbohydrate Research, Vol. 6 (1968) pp. 165–170. The partial hyrolysate of levan can be obtained by mild acid hydrolysis of levan and it is possible to obtain partially hydrolyzed levan with the main constituents having varying molecular weights. The varying conditions of hydrolysis and maximum molecular weights of the resulting partially hydrolyzed substances are given below where the maximum molecular weight means the molecular weight of molecules at the peak of chromatography. Measurement of the molecular weights was implemented with the HPLC (High Performance Liquid Chromatography) method (column: G2000 SWXL (Toso Co., Ltd.), eluent: 0.2M phosphate buffer (pH 6.8 ), detection: with a refractometer (RID=6 A Shimazu Seisakusho Co., Ltd.)).

| Hydrolysis conditions | | | Maximum molecular weight |
| --- | --- | --- | --- |
| pH 4.0, | 98° C., | 40 minutes | 1700 |
| pH 4.0, | 106° C., | 10 minutes | 2700 |
| pH 4.0, | 106° C., | 15 minutes | 1600 |
| pH 4.1, | 98° C., | 50 minutes | 1700 |
| pH 4.5, | 115° C., | 15 minutes | 2700 |

Next, the antihyperlipidemic effect and the effect of normalizing cholesterol metabolism of levan and partial hydrolysate of levan are described.

Note that for examples 1–7 described below, a hydrolysate which was obtained through hydrolysis at pH 4.0 and at a temperature of 106° C. for 15 minutes, was freeze-dried and used as a partial hydrolysate of levan.

Example 1

New Zealand White rabbits (male, body weights 1.2 to 1.4 kg) received 10 days of preparatory care prior to the testing. After that, a diet containing 1% cholesterol (manufactured by Oriental Yeast Kogyo Co., Ltd.) was fed to them for 3 weeks. Animals with a blood serum cholesterol value of 1800 mg/dl or higher were selected and divided into groups of 6 rabbits each. The administration of the specimen levan was initiated while the animals were fed with a normal diet (manufactured by Nippon Clair Co., Ltd.)

As a specimen, 100 mg of dried, powdered levan or partially hydrolyzed levan was put into gelatin capsules to be taken orally once a day. Empty gelatin capsules were given to the control group. Blood was taken from a vein in the ear every week and the blood serum was tested in the regular method and then the blood serum cholesterol value was measured using the enzymatic method (Determiner TC-555, Kyowa Medics Co., Ltd.). Eight weeks after the administration of the specimen began, the blood was taken in its entirety, drawn from the heart, and the animals were dissected. The aorta was extracted and opened and the lipid deposits were stained by oil red tinction to determine the occupancy ratio (%) of the stained area. The results are shown in Tables 1 and 2.

TABLE 1

| Animal group | Cholesterol value after administration of specimen (mg/dl) | | |
| --- | --- | --- | --- |
| | Week 0 | Week 4 | Week 8 |
| Control group | 2832 ± 193 | 555 ± 82 | 343 ± 58 |
| Levan group | 2923 ± 173 | 402 ± 52* | 225 ± 36* |
| Partial hydrolysate of levan group | 2903 ± 179 | 370 ± 64* | 211 ± 40* |

TABLE 1-continued

| Animal group | Cholesterol value after administration of specimen (mg/dl) | | |
| --- | --- | --- | --- |
| | Week 0 | Week 4 | Week 8 |

Mean value ± standard error
*There was a demonstrative difference at the level of significance of less than 5% for the control group.

TABLE 2

| Animal group | Lipid deposit-area ratio (%) |
| --- | --- |
| Control group | 57 ± 14 |
| Levan group | 22 ± 4* |
| Partial hydrolysate of levan group | 34 ± 6* |

Mean value ± standard error
Indicated as; mean value ± standard error
*There was a demonstrative difference at the level of significance of less than 5% for the control group.

From the above results, it is clear that levan and partial hydrolysate of levan have the effect of lowering blood serum cholesterol values and also have an effect of reducing deposition of lipids.

Example 2

10 week-old Fischer 344-type rats (male) were fed on a 20% fructose diet (fructose and regular feed(CE-2, manufactured by Nippon Clair Co., Ltd. ) were mixed at a weight ratio of 2:8) for four weeks. Water and the feed were taken freely. The animals given the specimen were in groups of 6 each and they were given a diet of 20% fructose to which the specimen. i.e., either levan or partial hydrolysate of levan in the form of dried powder, was added and mixed at a weight ratio of 1.5%. Four weeks later, blood was taken from a vein in the tail and triglyceride levels in the blood serum were measured using the enzymatic method. (Determiner; TG, manufactured by Kyowa Medics Co., Ltd.). The animals were dissected and the weight of adipose tissue in the vicinity of the testes was measured. The results are shown in Table 3.

TABLE 3

| Animal group | Blood serum triglyceride value (mg/dl) | Adipose tissue weight (g) |
| --- | --- | --- |
| Control group | 481 ± 11 | 5.3 ± 0.2 |
| Levan group | 320 ± 23* | 4.6 ± 0.2* |
| Partial hydrolysate of levan group | 337 ± 18* | 4.8 ± 0.4* |

Indicated as; mean value ± standard error
*There was a demonstrative difference at the level of significance of less than 5% for the control group.

From the above results, it is clear that levan and partial hydrolysate of levan have the effect of reducing lipids in the blood serum, and the effect of reducing adipose tissue.

Example 3

Levan or partially hydrolyzed levan was dissolved in water and forcibly administered using a probe to ICR-type mice (male and female, 5 each, weighing approximately 30 g). The dosage of levan was 0.15 g or that of partially hydrolyzed levan was 0.2 g. After this, the animals were observed for 14 days and no abnormalities were detected.

On the 14th day the animals were dissected and their body weights and the weights of various organs were measured. The organs were visually examined and no abnormalities were found. No biochemical abnormalities were observed in the blood.

From the results of examples 3 and 4, it is clear that no acute toxicity results from the ingestion of levan or partially hydrolyzed levan.

Example 4

ICR-type mice (male and female, 3 weeks old, groups of 10 each) were used in this experiment or levan and partially hydrolyzed levan were orally given at a dosage of 1 g/kg body weight every day for 24 weeks and no abnormalities were detected.

Example 5

F-344-type rats (male and female, 6 animals each, 6 weeks old) were fed on a diet containing 1% levan or a diet containing 1% of partially hydrolyzed levan for 6 months (25 weeks). During this time, no abnormalities in change (increase) of body weight, appearance or mobility were detected. After 6 months, dissection was performed to observe various organs and to investigate the biochemical condition of the blood and no abnormalities were found.

From the results of examples 5 and 6, it is clear that no chronic toxicity results from the ingestion of levan or partially hydrolyzed levan.

Example 6

Next, examples of applications for using the agent in the form of edible compositions are given. Neither the levan nor the partial hyrolysate of levan presented any problems of inhibiting sufficient ingestion as neither of them affected the taste or texture when they were prepared in any of the following forms (1–4).

(1) A solution containing 5% glucose, 10% reduced maltose and 2% citric acid was adjusted to pH 3.5 with potassium hydroxide, then 10% levan and 1% aromatic substance were added. After the mixture was thoroughly blended, it was put in 100 ml bottles and the bottles were sealed. After this, the mixture was heated at 100° C. for 30 minutes and left to cool to produce a low-calorie soft drink.

(2) Candy tablets were prepared using the following recipe:
Partial hydrolysate of levan; 10 kg.
Reduced maltose; 3 kg
Monoglyceride; 0.1 kg
Aromatic substance; 0.1 kg (3) A partial hydrolysate of levan was granulated by fluidized-bed granulation to be used as a topping for cakes and grapefruit at 1–2 grams per serving.

(4) Powdered levan or powdered partial hydrolysate of levan was dissolved in hot coffee at 1 w/v %

The above preparations (1)–(4) were served to 5 people and none complained of any unusual flavor.

What is claimed is;

1. A method for reducing lipids in a blood serum of a patient comprising administering an amount effective to reduce blood lipid levels of a levan obtained from *Streptococcus salivarius* or a levan material obtained from hydrolysis products of said levan with a maximum molecular weight of at least 1600 to said patient.

2. The method of claim 1 wherein said lipids comprise blood serum cholestorol.

3. The method of claim 1 wherein said lipids comprise blood serum triglyceride.

4. The method of claim 1 wherein said levan or levan material is administered orally.

5. A method of improving obesity symptom in a patient comprising administering an amount effective to improve obesity symptom of a levan obtained from *Streptococcus salivarius* or a levan material obtained from hydrolysis products of said levan with a maximum molecular weight of at least 1600 to said patient.

6. The method of claim 5 wherein said levan or levan material is administered orally.

7. A method for reducing lipids in a lipid deposit area of a patient comprising administering an amount effective to reduce lipids in said lipid deposit area of a levan obtained from *Streptococcus salivarius* or a levan material obtained from hydrolysis products of said levan with a maximum molecular weight of at least 1600 to said patient.

8. The method of claim 7 wherein said levan or levan material is administered orally.

9. A method for suppressing an increase in lipids in a blood serum, in a lipid deposit area, or in an adipose tissue of a mammal, comprising administering an amount effective to suppress an increase of lipids in a blood serum, in a lipid deposit area or in an adipose tissue of a levan obtained from *Streptococcus salivarius* or a levan material obtained from hydrolysis products of said levan with a maximum molecular weight of at least 1600 to said mammal.

10. The method of claim 9 wherein said levan or levan material is administered orally.

\* \* \* \* \*